(12) United States Patent
Sommer et al.

(10) Patent No.: US 8,219,213 B2
(45) Date of Patent: Jul. 10, 2012

(54) ACTIVE FIXATION CARDIAC VEIN MEDICAL LEAD

(75) Inventors: John L. Sommer, Coon Rapids, MN (US); Douglas N. Hess, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 807 days.

(21) Appl. No.: 11/324,075

(22) Filed: Dec. 30, 2005

(65) Prior Publication Data

US 2007/0156219 A1    Jul. 5, 2007

(51) Int. Cl.
*A61N 1/05* (2006.01)
(52) U.S. Cl. ...................................................... 607/127
(58) Field of Classification Search .................. 607/127, 607/131
See application file for complete search history.

(56) References Cited

U.S. PATENT DOCUMENTS

| | | | | |
|---|---|---|---|---|
| 4,233,992 A | * | 11/1980 | Bisping | 607/127 |
| 4,967,766 A | * | 11/1990 | Bradshaw | 607/127 |
| 5,246,014 A | | 9/1993 | Williams et al. | |
| 5,314,462 A | * | 5/1994 | Heil et al. | 607/128 |
| 5,456,708 A | * | 10/1995 | Doan et al. | 607/127 |
| 5,522,874 A | * | 6/1996 | Gates | 607/127 |
| 5,571,162 A | * | 11/1996 | Lin | 607/122 |
| 5,620,451 A | | 4/1997 | Rosborough | |
| 5,759,202 A | | 6/1998 | Schroeppel | |
| 5,837,006 A | | 11/1998 | Ocel et al. | |
| 5,871,531 A | | 2/1999 | Struble | |
| 6,006,122 A | | 12/1999 | Smits | |
| 6,078,840 A | | 6/2000 | Stokes | |
| 6,212,434 B1 | * | 4/2001 | Scheiner et al. | 607/123 |
| 6,256,541 B1 | * | 7/2001 | Heil et al. | 607/123 |
| 6,493,591 B1 | | 12/2002 | Stokes | |
| 6,871,085 B2 | | 3/2005 | Sommer | |
| 6,901,289 B2 | | 5/2005 | Dahl et al. | |
| 6,909,920 B2 | | 6/2005 | Lokhoff et al. | |
| 6,937,897 B2 | * | 8/2005 | Min et al. | 607/9 |
| 2004/0064172 A1 | * | 4/2004 | McVenes et al. | 607/122 |
| 2004/0068299 A1 | * | 4/2004 | Laske et al. | 607/3 |
| 2005/0085886 A1 | | 4/2005 | Hess et al. | |
| 2005/0246007 A1 | | 11/2005 | Sommer et al. | |

FOREIGN PATENT DOCUMENTS

WO    WO03030988 A2    4/2003

OTHER PUBLICATIONS

International Search Report, PCT/US2006/062609, Jun. 20, 2007, 6 Pages.

* cited by examiner

*Primary Examiner* — George Evanisko
(74) *Attorney, Agent, or Firm* — Reed A. Duthler; Stephen W. Bauer

(57) ABSTRACT

An implantable medical lead configured for active fixation in the vasculature of a patient includes an elongated lead body having a central lumen and a distal tip. Disposed within the central lumen are a fixation helix and an elongated member, such as a lead coil, coupled to the fixation helix. The elongated member is adapted to rotate the fixation helix, thereby causing it to advance or retract within the central lumen of the lead body. The lead body includes a window along a portion of its length through which the fixation helix may be affixed to a blood vessel of the patient's vasculature.

27 Claims, 4 Drawing Sheets

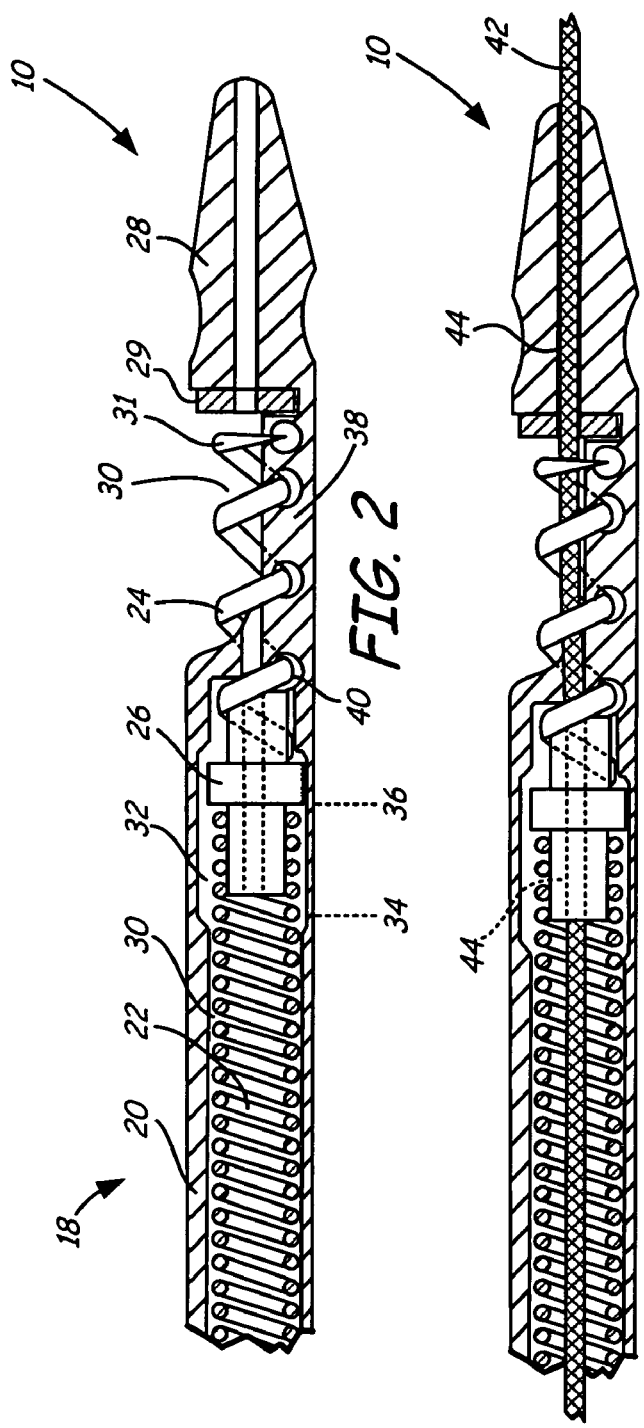
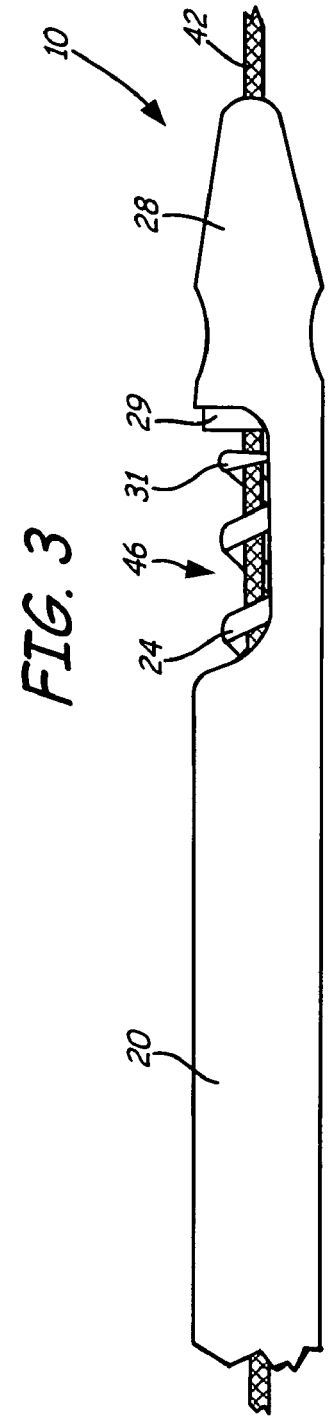

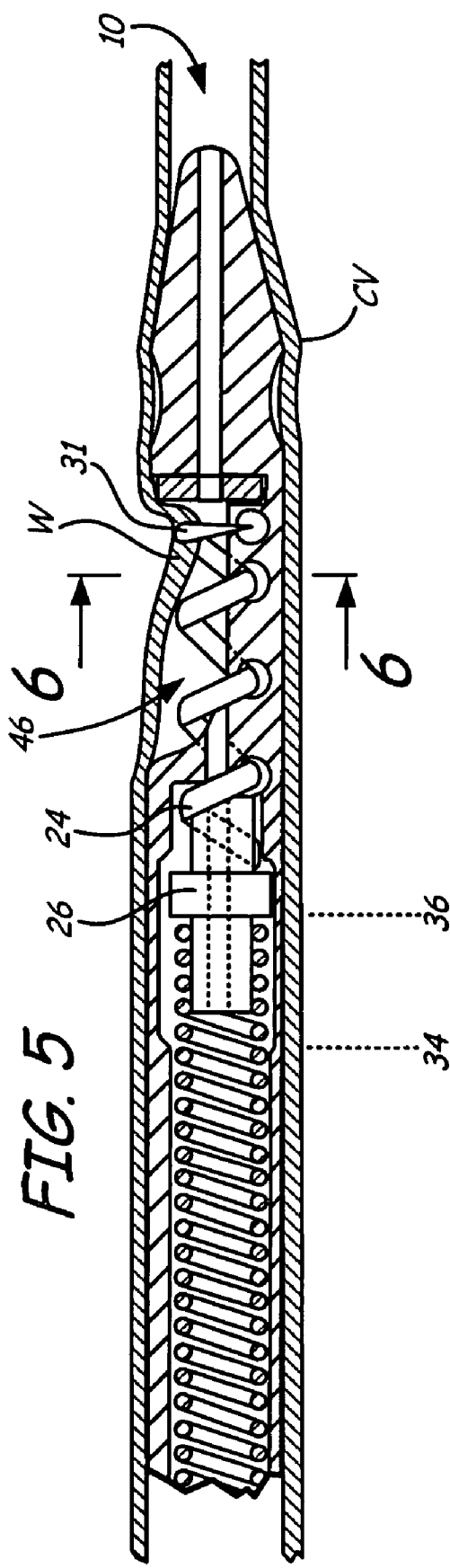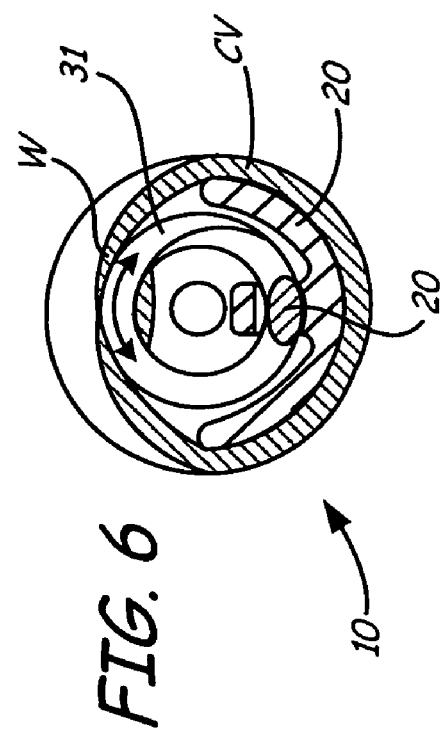

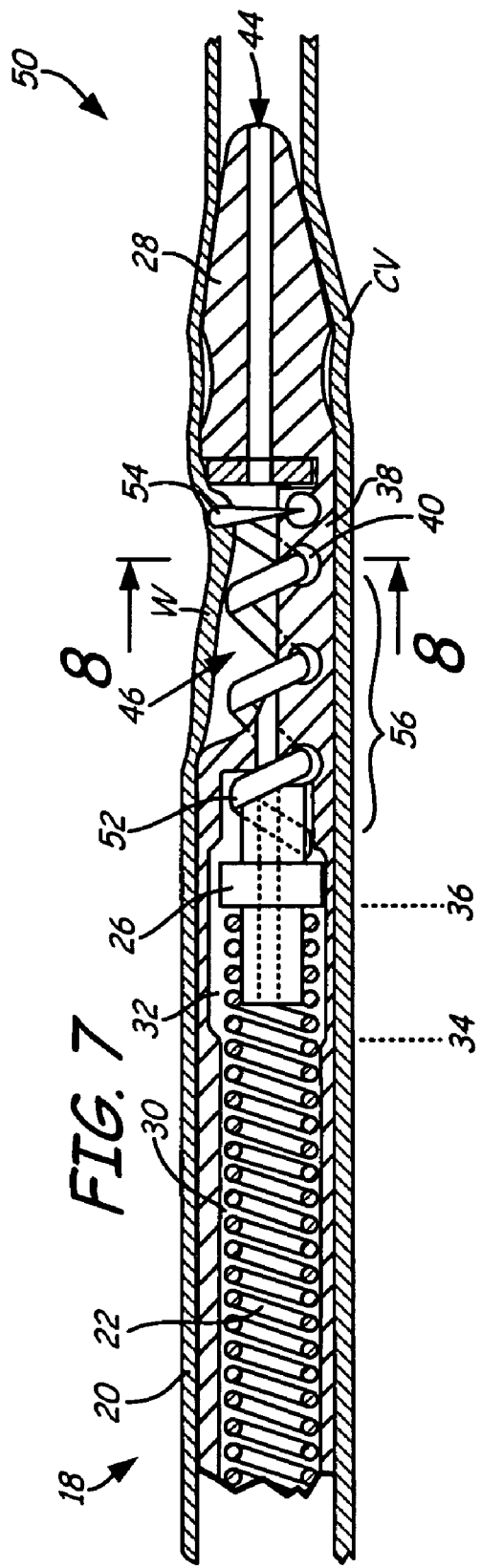
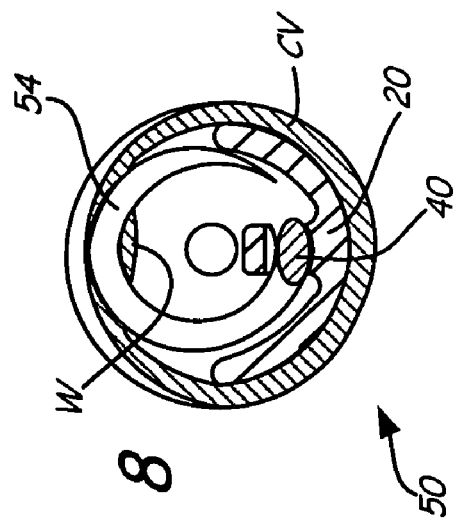

ACTIVE FIXATION CARDIAC VEIN MEDICAL LEAD

BACKGROUND OF THE INVENTION

The present invention relates generally to the field of implantable medical devices, and more particularly, to an implantable medical lead configured for active fixation in a cardiac vein of a patient.

Implantable medical leads are used with a wide variety of medical devices to provide electrical and/or mechanical connections between the device and a location within the body. For example, implantable medical leads are commonly used with pacemakers, cardioverters, and defibrillators to provide an electrical connection between the device and an electrode positioned within or adjacent the heart. Recently becoming more prevalent are medical leads that are configured to be advanced from the right atrium of the heart through the coronary sinus into a cardiac vein for sensing electrical activity in or providing electrical stimulation to the left ventricle of the heart. As with many implantable medical leads, it is generally preferred that a placement of the lead within the vasculature be fixed.

BRIEF SUMMARY OF THE INVENTION

The disclosures relate to an implantable medical lead configured for active fixation in the vasculature of a patient. The medical lead includes an elongated lead body having a central lumen and a distal tip. Disposed within the central lumen are a fixation helix and an elongated member, such as a lead coil, coupled to the fixation helix. The elongated member is adapted to rotate the fixation helix, thereby causing it to advance or retract within the central lumen of the lead body. The lead body includes a window along a portion of its length through which the fixation helix may be affixed to a blood vessel of the patient's vasculature.

BRIEF DESCRIPTION OF THE DRAWINGS

FIG. 2 is a cross-sectional side view of a medical lead in accord with the present invention.

FIG. 3 is a cross-sectional side view of the medical lead shown in FIG. 2 as positioned about a guidewire.

FIG. 4 is a side view of the medical lead shown in FIG. 2.

FIG. 5 is a cross-sectional side view of the medical lead shown in FIG. 2 as affixed to a wall of the cardiac vein.

FIG. 6 is a view of cross-section 6-6 of FIG. 5.

FIG. 7 is a cross-sectional side view of a medical lead in accord with the present invention as affixed to a wall of a cardiac vein.

FIG. 8 is a view of cross-section 8-8 of FIG. 7.

DETAILED DESCRIPTION

Figure 1:
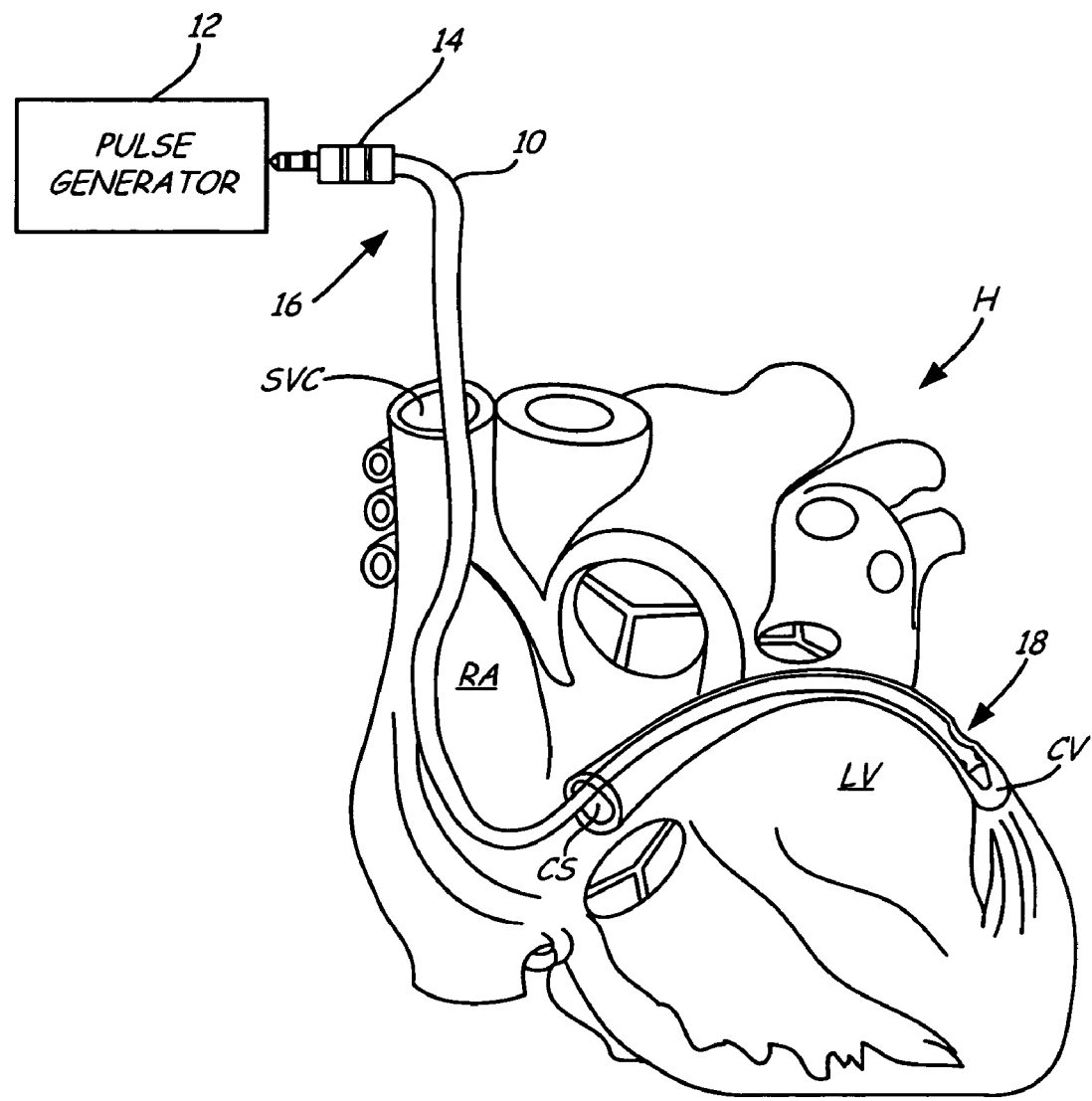
FIG. 1 is a perspective view of an implantable medical lead in accord with the present invention as implanted in a cardiac vein.

FIG. 1 is a perspective view of implantable medical lead 10 in accord with the present invention. As shown in FIG. 1, medical lead 10 is used with pulse generator 12, which may be a cardiac pacemaker or a cardioverter/defibrillator, for providing therapy to and/or sensing electrical activity in heart H. Alternately, medical lead 10 may be used with any type of medical device that requires an electrical and/or a mechanical connection to a location within the vasculature of the body. To that end, the function and composition of pulse generator 12 will vary depending upon its intended function.

Medical lead 10 includes connector assembly 14 at a proximal end 16 opposite distal end 18. Connector assembly 14 couples medical lead 10 to pulse generator 12 as is well known in the art. In the embodiment of FIG. 1, medical lead 10 extends from pulse generator 12, through superior vena cava SVC into right atrium RA of heart H, and then through coronary sinus CS into cardiac vein CV. As will be described in greater detail below, medical lead 10 includes structure at distal end 18 for fixing distal end 18 to an implant site within cardiac vein CV that is in a plane generally parallel to a longitudinal axis of medical lead 10. In the embodiment illustrated in FIG. 1, this fixation structure doubles as an electrode that is fixed to a left ventricular epicardial site of heart H for sensing electrical activity in and providing electrical stimulation to left ventricle LV of heart H.

FIG. 2 is a cross-sectional side view of distal end 18 of implantable medical lead 10. As shown in FIG. 2, medical lead 10 is formed of elongated body 20, lead conductor 22, fixation helix 24, connection sleeve 26, distal tip 28, and monolithic controlled-release device (MCRD) 29.

Elongated body 20 extends from connector assembly 14 to distal tip 28 and is preferably formed of a biocompatible plastic such as polyurethane or silicone rubber. Elongated body 20 functions as an insulating sleeve in which many of the electrical and mechanical elements of medical lead 10 are protected. Accordingly, elongated body 20 includes central lumen 30 in which elongated lead conductor 22, fixation helix 24, and connection sleeve 26 are all disposed.

Lead conductor 22 extends between proximal and distal ends 16 and 18 of medical lead 10. At proximal end 16, lead conductor 22 is electrically coupled to connector assembly 14 for electrical connection with pulse generator 12. At distal end 18, lead conductor 22 is electrically and mechanically coupled to fixation helix 24 via connection sleeve 26 via crimping, welding, or other conventional means. Lead conductor 22 is adapted to rotate fixation helix 24, thereby advancing and/or retracting fixation helix 24 within central lumen 26 of elongated body 20. Mechanisms for moving fixation helix 24 are well known to those skilled in the art, but are typically activated at proximal end 18 of medical lead 10 via a rotating connector pin coupled thereto. As shown in FIG. 2, lead conductor 22 is a coiled conductor, but alternately may take the form of a stranded or cabled conductor.

Fixation helix 24 functions both as a structure for actively fixing a placement of medical lead 10 within cardiac vein CV and as an electrode to which pacing pulses may be delivered and cardiac electrical function can be sensed by pulse generator 12. Fixation helix 24 is a helical structure coupled to connection sleeve 26 at a proximal end via crimping, welding, or other conventional means and having sharpened, chiseled tip 31 at its distal end. In use, fixation helix 24 is rotated to embed chiseled tip 31 into a wall of cardiac vein CV as more fully described below. Materials for forming fixation helix 24 include, but are not limited to, platinum, iridium, titanium, nickel, and platinum-iridium alloys. In embodiments where fixation helix 24 does not function as an electrode (e.g., where medical lead 10 is used only to deliver a therapeutic agent to a desired location within the vasculature), materials for forming fixation helix 24 may further include without limitation polycarbonate, polypropylene, synthetic resins and superelastic materials, such as Nitinol.

Connection sleeve 26 electrically and mechanically couples elongated lead conductor 22 and fixation helix 24. Connection sleeve 26 is preferably formed a conductive material to impart electrical connectivity between lead conductor 22 and fixation helix 24. For embodiments in which fixation helix does not function as an electrode, however, connection sleeve 26 may be formed of any body-implantable material. In alternate embodiments, connection sleeve 26 may be omitted and fixation helix 24 may be configured for direct connection to lead conductor 22.

In the embodiment illustrated in FIG. 1, elongated body 20 includes motion limiting portion 32 which cooperates with connection sleeve 26 to define a range of motion for fixation helix 24 within central lumen 30. In this embodiment, a diameter of central lumen 30 in portion 32 is greater than a diameter of central lumen 30 on either side of portion 32. This variation in diameters prevents connection sleeve 26 from being retracted further than retracted stop position 34 or advanced further than extended stop position 36. This in turn restricts motion of fixation helix 24 attached to connection sleeve 26.

Elongated body 20, as shown in FIG. 2, also includes retention structure 38 protruding into central lumen 30 and having retention holes 40 therethrough. In this embodiment, fixation helix 24 is threaded through retention holes 40 to maintain fixation helix 24 within central lumen 30 as medical lead 10 is advanced into cardiac vein CV.

Distal tip 28 extends axially from elongated body 24. Distal tip 28 of medical lead 10 is configured to aid the surgeon in navigating medical lead 10 during implant to a desired location within the cardiac vasculature. Distal tip 28 is preferably formed of a biocompatible plastic such as polyurethane or silicone rubber.

MCRD 29 is optionally included in distal end 18 of medical lead 10 for eluting an anti-inflammatory agent, such as a steroid, following fixation of medical lead 10. In FIG. 2, MCRD 29 is formed in a disk proximate fixation helix 24 and distal tip 28. Other embodiments of the present invention may exclude MCRD 29 or may incorporate other methods of delivering an anti-inflammatory agent proximate the fixation site.

FIG. 3 illustrates an exemplary method for advancing medical lead 10 into the vasculature of a patient. In particular, FIG. 3 is a cross-sectional side view of medical lead 10 as positioned about guidewire 42. In the embodiment illustrated in FIG. 3, guidewire 42 is navigated using known techniques into cardiac vein CV intended for implant of medical lead 10. Once guidewire 42 is in place, medical lead 10 is advanced over guidewire 42 into cardiac vein CV. To accommodate this navigation process, medical lead 10 includes guidewire lumen 44 which extends through central lumen 30 of elongated body 20 and through distal tip 28. In some embodiments of the present invention, a silicone rubber seal may be included at a distal end of distal tip 28 to minimize fluid flow into guidewire lumen 44.

During implant, guidewire 42 may further be used to help maintain fixation helix 24 within central lumen 30 of elongated body 20. Prior to guidewire 42 being retracted from guidewire lumen 44, guidewire 42 is centrally positioned through fixation helix 24 and will prevent substantially movement of fixation helix 24 out of central lumen 30. The use of guidewire 42 for this purpose may be in addition to or in lieu of the use of retention structure 38 for the same purpose.

FIG. 4 is a side view of distal tip 18 of medical lead 10. As shown in FIG. 4, elongated body 20 includes attachment window 46 for exposing fixation helix 24 to a wall of cardiac vein CV. In the example shown in FIG. 4, attachment window 46 extends partially around an outer surface of elongated body 20 in a direction substantially transverse to a longitudinal axis of medical lead 10 (e.g., attachment window 46 is not annular in cross-section, as also illustrated by FIG. 6). As a result, at least a portion of an outer surface of elongated body 20 shields a circumferential portion of helix 24. As described in further detail below, elongated body 20 may substantially block passage of electrical signals between the shielded portion of fixation helix 24 and patient tissue in examples in which fixation helix 24 is used as a pacing electrode/sensor. As shown in FIG. 4, at least one circumferential outer surface portion of helix 24 is exposed to patient tissue by attachment window 24 and an opposing outer surface portion of helix 24 is shielded from patient tissue by elongated body 20. That is, helix 24 comprises a portion that extends in a direction substantially parallel to a longitudinal axis of medical lead 10, where a section of that portion is exposed by attachment window 46, and elongated body 20 may block at least some of the electrical signals provided to another section of the portion of helix 24 that that extends in a direction substantially parallel to a longitudinal axis of medical lead 10. As will be described more fully below with reference to FIGS. 5 and 6, attachment window 46 allows for an implant site in cardiac vein CV that is substantially parallel to a longitudinal axis of medical lead 10.

FIG. 5 is a cross-sectional side view of medical lead 10 as affixed to wall W of cardiac vein CV, while FIG. 6 is a view of cross-section 6-6 of FIG. 5. During implant of medical lead 10 into cardiac vein CV, walls W of cardiac vein CV will contract about medical lead 10, with walls W of cardiac vein CV adjacent attachment window 46 moving into attachment window 46. To better insure this contraction occurs, an electrical voltage may be applied between fixation helix 24 and a second electrode (not illustrated) carried either on medical lead 10 or pulse generator 12 just prior to affixation of either on medical lead 10 or pulse generator 12 just prior to affixation of medical lead 10 to cause cardiac vein CV to constrict.

To prevent the inadvertent piercing of unintended body tissues, fixation helix 24 (and connection sleeve 26) is preferably in retracted stop position 34 with chiseled tip 31 pointed toward away from attachment window 46. Once medical lead 10 has been advanced to its final position, fixation helix 24 (and connection sleeve 26) is rotated to cause fixation helix 24 (and connection sleeve 26) to be advanced toward extended stop position 36 and chiseled tip 31 to engage wall W of cardiac vein CV—thus affixing helix 24 to wall W.

When fixation helix 24 is to be used as a pacing electrode/sensor for left ventricle LV, it is generally preferred that fixation helix 24 be affixed to the myocardial (or left ventricular) side of cardiac vein CV rather than the pericardial side of cardiac vein. Attachment window 46 and fixation helix 24 provide a simple method for ensuring that medical lead 10 is oriented in this preferred direction. Fixation helix 24 can be used to sense electrical signals generated by the heart. Thus, by monitoring the strength of those detected signals, it can be determined when attachment window 46 is most oriented toward left ventricle LV.

This configuration further allows for implantable medical lead 10 to be used to provide a shielded, or directional, pacing signal. This results because electrical signals provided to fixation helix 24 will be substantially blocked by elongated body 20 while passing through attachment window 46. Thus, pacing signals may be directed to left ventricle LV, while minimizing stimulation of the patient's phrenic nerve.

FIG. 7 is a cross-sectional side view of distal end 18 of medical lead 50 as affixed to wall W of cardiac vein CV, while FIG. 8 is a view of cross-section 8-8 of FIG. 7. Elements common to both medical lead 10 of FIGS. 1-6 and medical lead 50 of FIGS. 7-8 are similarly numbered in FIGS. 7-8. Like medical lead 10, medical lead 50 is formed of elongated body 20, lead conductor 22, connection sleeve 26, distal tip 28, and MCRD 29. Elongated body 20 includes central lumen 30, motion limiting portion 32 (for providing retracted stop position 34 and extended stop position 36), retention structure 38 with retention holes 40, guidewire lumen 44 for receipt of guidewire 42 (not shown in FIGS. 7 and 8), and attachment window 46. The description of each of these elements above applies equally to the embodiment illustrated in FIGS. 7-8.

Medical lead 50, however, presents a minor variation on medical lead 10. In particular, medical lead 50 includes fixation helix 52 having distal-most coil 54 off center of, or with a greater diameter than, remaining coils 56. This configuration of fixation helix 52 result in easier engagement of wall W of cardiac vein CV during its affixation thereto. This configuration may further allow for greater penetration of wall W, thus providing better contact with the myocardial tissue of heart H.

Although the present invention has been described with reference to preferred embodiments, workers skilled in the art will recognize that changes may be made in form and detail without departing from the spirit and scope of the invention.

The invention claimed is:
1. An implantable medical lead comprising:
a distal tip;
an elongated body coupled to the distal tip, the elongated body comprising a lumen therethrough and an attachment window proximate the distal tip that exposes a portion of the lumen, wherein the attachment window comprises a proximal end and a distal end and extends partially, but not fully, around an outer surface of the elongated body, between the proximal end and the distal end of the attachment window;
an elongated lead element carried within the lumen; and
a rotatable fixation helix carried within the lumen proximate the attachment window, the fixation helix having a proximal end coupled to the lead element and a tip at a distal end for engaging an implant site proximate the attachment window, and wherein the fixation helix rotates to advance the distal end of the fixation helix towards the distal end of the attachment window, and wherein the fixation helix is movable between a retracted position and an extended position past which the fixation helix cannot be advanced, and wherein a portion of the distal end of the fixation helix is retained within the elongated body when the fixation helix is in the extended position.

2. The implantable medical lead of claim 1 and further comprising a connection sleeve coupled between the lead element and the fixation helix.

3. The implantable medical lead of claim 2, wherein the elongated body comprises a motion limiting portion in which the connection sleeve is positioned to define a range of motion for the connection sleeve.

4. The implantable medical lead of claim 1, wherein the elongated body is formed of a biocompatible plastic.

5. The implantable medical lead of claim 1, wherein the elongated lead element comprises a conductor.

6. The implantable medical lead of claim 1, wherein the elongated lead element comprises a coiled conductor.

7. The implantable medical lead of claim 1, wherein the elongated lead element is adapted to rotate the fixation helix to advance or retract the fixation helix within the central lumen of the elongated body.

8. The implantable medical lead of claim 1, wherein the fixation helix comprises an electrode.

9. The implantable medical lead of claim 1, wherein the fixation helix is formed of a material selected from the group consisting of platinum, iridium, titanium, nickel, and alloys made substantially thereof.

10. The implantable medical lead of claim 1, wherein a distal-most coil of the fixation helix is off-center from a plurality of remaining coils of the fixation helix.

11. The implantable medical lead of claim 1 and further comprising a monolithic controlled-release device positioned proximate the fixation helix and the distal tip.

12. The implantable medical lead of claim 1, wherein the elongated body further comprises a retention structure that protrudes into the attachment window and includes a retention hole through which the fixation helix may be thread.

13. The implantable medical lead of claim 1 and further comprising a guidewire lumen extending through both the lumen and the distal tip for receipt of a guidewire.

14. The implantable medical lead of claim 1, wherein a first portion of the fixation helix is exposed by the attachment window and the outer surface of the elongated body electrically shields a second portion of the helix substantially opposite the first portion.

15. The implantable medical lead of claim 1, wherein a distal-most coil of the fixation helix comprises a greater diameter than a plurality of remaining coils of the fixation helix.

16. An implantable medical lead comprising:
an elongated body extending between a proximal end and a distal end, and including an attachment window that comprises a proximal end and a distal end, wherein the attachment window extends partially, but not fully, around an outer surface of the elongated body between the proximal end and the distal end of the attachment window;
a fixation helix disposed within the elongated body and movable through the elongated body between a retracted position and an extended position past which the fixation helix cannot be advanced, wherein a distal end of the fixation helix moves towards the distal end of the attachment window when the fixation helix moves from the retracted position to the extended position, and wherein a portion of the distal end of the fixation helix is retained within the elongated body when the fixation helix is in the extended position.

17. The implantable medical lead of claim 16, wherein the elongated body further comprises:
a central lumen extending through the elongated body and at least partially exposed through the attachment window, wherein the fixation helix is disposed within the central lumen; and
an elongated lead element disposed within the central lumen and coupled to the fixation helix.

18. The implantable medical lead of claim 16, wherein a distal-most coil of the fixation helix is off-center from a plurality of remaining coils of the fixation helix.

19. The implantable medical lead of claim 16, and further comprising a guidewire lumen extending through the elongated body.

20. The implantable medical lead of claim 16, wherein when the fixation helix is proximate the attachment window, a first portion of the fixation helix is exposed and a second portion of the helix substantially opposite the first portion is electrically insulated by the outer surface of the elongated body.

21. The implantable medical lead of claim 16, wherein a distal-most coil of the fixation helix comprises a greater diameter than a plurality of remaining coils of the fixation helix.

22. An implantable medical lead configured to affix to a cardiac vein, the implantable medical lead comprising:
   a first elongated body including an attachment window configured to receive a part of a wall of the cardiac vein, wherein the attachment window comprises a proximal end and a distal end and extends partially, but not fully, around an outer surface of the first elongated body between the proximal end and the distal end of the attachment window; and
   a fixation helix including a distal tip and disposed within the first elongated body, the distal tip being configured to engage with the part of the wall of the cardiac vein received in the attachment window as the fixation helix rotates within the first elongated body to advance the distal tip of the fixation helix toward the distal end of the attachment window; and
   wherein the fixation helix is movable through the elongated body between a retracted position and an extended position past which the fixation helix cannot be advanced and wherein a portion of the distal end of the fixation helix is retained within the elongated body when the fixation helix is in the extended position.

23. The implantable medical lead assembly of claim 22, and further comprising:
   a second elongated body configured to move the fixation helix between a retracted position and an extended position.

24. The implantable medical lead of claim 22, wherein the first elongated body is configured to receive a fluid delivery lumen.

25. The implantable medical lead of claim 22, wherein a distal-most coil of the fixation helix comprises a greater diameter than a plurality of remaining coils of the fixation helix.

26. An implantable medical lead comprising:
   an elongated body extending from a proximal end to a distal end, the elongated body comprising a lumen extending therethrough;
   a fixation helix located within the lumen, the fixation helix comprising a proximal end coupled to an elongated element and a distal end, wherein rotation of the fixation helix advances the distal end of the fixation helix towards the distal end of the elongated body; and
   an attachment window formed in the elongated body, wherein the attachment window comprises a proximal end and a distal end, wherein the attachment window extends partially, but not fully, around an outer surface of the elongated body between the proximal end and the distal end of the attachment window;
   wherein, after the fixation helix is advanced into the portion of the elongated body occupied by the attachment window, the fixation helix comprises an exposed portion facing towards the attachment window, and wherein the fixation helix comprises a shielded portion facing away from the attachment window, wherein the exposed portion and the shielded portion are located on opposite sides of the fixation helix; and
   wherein the fixation helix is movable through the elongated body between a retracted position and an extended position past which the fixation helix cannot be advanced and wherein a portion of the distal end of the fixation helix is retained within the elongated body when the fixation helix is in the extended position.

27. An implantable medical lead comprising:
   an elongated body extending from a proximal end to a distal end and defining a length, the elongated body comprising a lumen extending therethrough;
   a fixation helix located within the lumen, the fixation helix comprising a proximal end coupled to an elongated element and a distal end; and
   an attachment window formed in the elongated body along a portion of the length of the elongated body, wherein the attachment window comprises a proximal end and a distal end, wherein the attachment window extends partially, but not fully, around the portion of the elongated body between the proximal end and the distal end of the attachment window; and
   wherein the fixation helix is movable through the elongated body between a retracted position and an extended position past which the fixation helix cannot be advanced and wherein a portion of the distal end of the fixation helix is retained within the elongated body when the fixation helix is in the extended position.

\* \* \* \* \*